United States Patent [19]

Gettleman et al.

[11] Patent Number: 4,661,065
[45] Date of Patent: Apr. 28, 1987

[54] SOFT DENTURE LINER

[75] Inventors: Lawrence Gettleman, Metairie, La.; Paul H. Gebert, Pensacola, Fla.

[73] Assignee: Gulf South Research Institute, Baton Rouge, La.

[21] Appl. No.: 804,837

[22] Filed: Dec. 4, 1985

[51] Int. Cl.[4] .................. A61C 13/02; A61K 6/00
[52] U.S. Cl. .................... 433/168.1; 264/17; 427/2; 433/171; 433/199.1; 523/120
[58] Field of Search ............ 523/120; 528/399; 433/168.1, 171, 199.1; 427/2; 264/17

[56] References Cited

U.S. PATENT DOCUMENTS

| | | | |
|---|---|---|---|
| 3,945,966 | 3/1976 | Vicic et al. | 528/399 |
| 4,432,730 | 2/1984 | Gettleman et al. | 523/120 |
| 4,543,379 | 9/1985 | Gettleman et al. | 523/120 |

Primary Examiner—Lorenzo B. Hayes
Attorney, Agent, or Firm—Jean A. Buttmi; Martin P. Hoffman; Mitchell B. Wasson

[57] ABSTRACT

The invention provides a denture liner composition for a composite denture based on a phosphonitrilic fluoroelastomer [poly(fluoroalkoxy)phosphazene] curable at atmospheric pressure at temperatures of about 100° C. or less, conveniently by immersing the packed denture flask in a water bath at the appropriate temperature. The composition includes trimethacrylate and dimethacrylate cross-linking agents for increasing liner hardness and decreasing water sorption characteristics of the cured liner. The composition preferably further includes filler materials for increasing the hardness of the liner product. The composite denture is preferably prepared in a one-step process wherein the liner composition material of a single firmness is cured in situ with the denture base material. Alternatively, a firm liner material is cured at the periphery of the denture, and a softer liner material cured at the center; this provides a firm elastic liner adjustable by grinding where soft tissues must be displaced, and a soft elastic liner over bony anatomy, where stresses from chewing are most concentrated and soft tissues are thin. Another possibility lies in curing the soft liner directly to a precured denture as a reline procedure in an pre-existing denture.

38 Claims, No Drawings

SOFT DENTURE LINER

GRANT INFORMATION

The development of the invention was supported by the National Institute of Dental Research through Research Grant Number R01 DE-04814.

BACKGROUND OF THE INVENTION

Removable prosthetic dentures typically consist of a baseplate of hard poly(methyl methacrylate) which supports the artificial teeth needed for chewing and for esthetics. Many patients have difficulty tolerating a hard denture so there is a need for a soft liner affixed to the denture base to cushion the soft tissue. A number of criteria have been established for materials to be useful as denture liners, notably non-toxicity and non-allergenicity. The best materials should be permanently resilient, inert, cleanable, substantially water-insoluble, have low water sorption characteristics and good tensile and bond strengths. While softness is desirable for comfort, the liner material must be sufficiently firm to displace the soft tissues of the mouth and to allow grinding of the denture periphery to avoid creating sore spots on the tissues; additionally, the liner material must be permanently bondable to the denture base material. It is also preferable from a practical standpoint that the lined denture be capable of fabrication under conditions generally found in dental laboratories or in a dentist's office, avoiding extremes of temperature and pressure conditions, or the use of special equipment.

Several liner materials have been proposed which satisfy these criteria sufficiently to be useful, such as silicone rubbers, plasticized poly(methacrylates), polyurethanes and polyvinyl chlorides. An especially useful liner material is disclosed in U.S. Pat. No. 4,251,215 issued on Feb. 17, 1981 to May et al, comprising phosphonitrilic fluoroelastomer (poly(fluoroalkoxy)phosphazene) which exhibits particularly good resiliency and biocompatibility characteristics. The fluoroelastomer liner materials exemplified therein, however, have been found to be somewhat deficient with respect to tensile strength, hardness, water-sorption and bondability to denture base material, as compared to the theoretical ideal. Further, the process for forming the denture as described in the May et al patent is a two-step process which requires the liner and denture base to be separately cured, and additionally requires the use of strong bonding agents, as well as the use of temperatures in excess of 100° C. (boiling point of water at atmospheric pressure) for curing the liner. The fabrication of this prior art composite denture thus requires somewhat elaborate equipment, and cannot be conveniently accomplished in an average dental office or laboratory.

In order to overcome the drawbacks of such prior art compositions, liner compositions of the type described in U.S. Pat. No. 4,432,730 to Gettleman et al, filed Oct. 1, 1982 and incorporated herein by reference, have been proposed. While such dental liner compositions have proved generally satisfactory, water sorption tendencies of the cured liner material according to the Gettleman et al patent have been higher (4-5% w/w) than desirable for optimum use in the mouth. This composition also used methyl methacrylate (MMA) monomer, which is volatile and therefore difficult to control prior to curing; hardness and water sorption properties of these prior art compositions have been found to be highly dependent upon the proper amount of MMA. It is thus desirable to decrease water sorption characteristics and concomitant swelling of this prior art dental liner material, in order to improve dimensional stability of the product liner material over time.

SUMMARY OF THE INVENTION

The invention accordingly provides an improved denture liner composition based on phosphonitrilic fluoroelastomers [poly(fluoroalkoxy)phosphazene] which, when cured by cross-linking of pendant groups, retain the excellent elastic properties of the fluoroelastomer base material, while exhibiting improved water sorption characteristics, hardness, tensile strength, grinding and adjusting ability, and bond strength. The denture liner composition is curable at or below temperatures of 100° C. at atmospheric pressure, and retains dimensional stability during curing. The composite denture is preferably formed by curing the shaped liner material in situ, that is, placed directly against a conventional denture base dough which may be partially cured, or as a reliner to an existing denture. The packed denture flask is conveniently immersed in an open water bath at temperatures appropriate to cure the denture base and liner, no higher than 100° C., in order to cure the liner and denture base together. The method improves the bond strength of the finished composite denture, and obviates the use of potentially harmful bonding agents such as sulfuric or perfluoroacetic acid or epoxy or urethane adhesives. Most importantly, the method avoids the use of high temperatures and/or pressurized equipment, and can thus be used in commercial dental laboratories or even in the dentist's office. Additionally, the use of the relatively low temperatures avoids vaporization of any volatile monomers present and prevents dehydration of the liner material during curing. Vaporization produces porosity in the denture base and the liner and dehydration necessitates rehydration of the entire denture prior to us in the intended aqueous environment, and the dehydration/rehydration steps may cause undesirable dimensional changes in the liner as well as the substrate denture base.

Broadly, the denture liner composition of the invention comprises a phosphonitrilic fluoroelastomer in combination with at least one di- and trimethacrylate cross-linking agent to improve hardness and decrease water sorbtion of the cured product liner. These ingredients also function to provide an interpenetrating polymer network which improves tensile strength while not affecting hardness, and decreases water sorption tendencies. Preferred difunctional agents include a dimethacrylate glycol ester cross-linking agent, especially polyethylene glycol dimethacrylate (PEGDMA), 1,6-hexamethylene glycol dimethacrylate (HGDMA), ethylene glycol dimethacrylate (EGDMA), or tetraethylene glycol dimethacrylate (TEGDMA) to improve tensile strength and bond strength of the product liner; EGDMA, particularly increases hardness and improves workability and packing properties of the uncured liner. Trimethylopropane trimethacrylate (TMP-TMA) is a particularly effective trifunctional cross-linking agent. Fillers such as particles of a hard acrylic resin, silica, $Al_2O_3$, diatomaceous earth, or $BaSO_4$ are also desirably included to increase hardness and improve the packing ability of the dough, grinding and adjusting properties of the cured liner, and radiopacity in the case of $BaSO_4$. The composition further optimally includes additives to facilitate curing of the liner material by growth of an interpenetrating network of acrylic moieties which crosslink with the preformed polyphosphazine chains at temperatures at or below 100° C., particularly benzoyl peroxide or lauroyl peroxide as free-radical initiators. Lauroyl peroxide is particularly useful because it helps to plasticize the elastomer. The following materials, in admixture, are within the scope of the invention:

| Material | | Percent by Wt. of Total Composition | |
|---|---|---|---|
| | | Useful | Preferred |
| Phosphonitrilic fluoroelastomer | | 30 to 90 | 30 to 60 40 to 90 |
| Trimethacrylate cross-linker | ⎫ | 5 to 20 | 18 to 20 |
| Dimethacrylate cross-linker | ⎬ Interpenetrating Network | 0.5 to 20 | 2 to 4 (EGDMA) |
| Filler | ⎭ | 0 to 15 | 10 to 12 |
| Initiator | | 0.5 to 1.0 | 1.0 (lauroyl peroxide) |
| Piqment | | 0 to 0.5 | 0.1 to 0.2 (CdSSe) |

If TMP-TMA and EGDMA are employed, a TMP-TMA/EGDMA ratio of from about 40:1 to 1:4 is generally adequate. While a ratio of from about 10:1 to 9:2 is preferred, increasing EGDMA relative to TMP-TMA can result in an increase in water sorption. A TMP-TMA/EGDMA ratio of about 9:2 is generally preferred. It is contemplated that comparable trimethacrylate/dimethacrylate ratios are employable with other di- and tri-functional methacrylates.

The liner of the invention is curable in situ when applied to a conventional denture base dough, typically an acrylic dough, such as a freshly packed or partially cured poly(methyl methacrylate); the base and liner are thus cured together. The liner may also be cured in situ on a cured base, which would typically be desirable when a pre-existing denture is being relined. In both instances, adhesion of liner to base is usually promoted if the denture base is first wetted with a $C_1$–$C_6$ alkyl monomethacrylate, especially methyl methacrylate (MMA).

DETAILED DESCRIPTION OF THE INVENTION

The dental liner composition of the invention is based on phosphonitrilic fluoroelastomers (poly(fluoroalkoxy)phosphazenes) of the type described in U.S. Pat. Nos. 3,702,833 and 3,888,799, both to Rose et al. The polymers are characterized by repeating units of the general formula

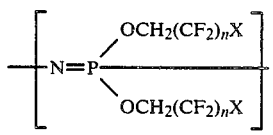

wherein X is H or F, and n is usually from 1 to 11. Such elastomers are commercially available, and are typified by compounded PNF-200, previously available from Firestone Central Research Laboratories, 1200 Firestone Parkway, Akron, Ohio, and now available from Ethyl Corporation, Baton Rouge, LA, and sold as EYPEL-F. This material is represented as

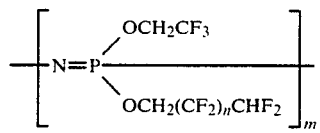

wherein n is 3, 5, 7, 9 or 11, and m is from 10,000 to 50,000, and described as a thermoset. A comercially-available compounded product, PNF-200 (Firestone) is reported to have the following properties:

| | |
|---|---|
| Color | Amber |
| Specific Gravity | 1.75 to 1.85 |
| Mooney Viscosity | 15 |
| Solvents | Ketones, THF, DMF |
| Glass Transition Temperature | −68° C. (−90° F.) |
| Durometer A Hardness | 35–90 |
| Tensile Strength | 6.9–13.8 MPa (1000–2000 lbf/in$^2$) |
| 100% Modulus | 2.8–13.8 MPa (400–2000 lbf/in$^2$) |
| Elongation | 75–250% |
| Tear Resistance | 43,800 N/m (250 lbf/in) |

Preferably, the fluoroelastomer is purified by extraction and coagulation from acetone in a known manner prior to biomedical use in the liner composition of the invention.

The elastomer is employed in amounts of from about 30% to about 90% by weight of the total denture liner composition, usually from about 30% to 60% for a firm liner material, and from about 40% to about 90% for a soft liner material.

It is noted that PNF-200, as commercially obtained from the manufacturer, Firestone, contains residual amounts of NaCl, nominally less than about 0.05% w/w. The presence of NaCl adversely affects water sorption characteristics of the compounded elastomer, and it is thus important that the elastomer be purified of this contaminant. This may readily be accomplished by dissolving the raw gum in reagentgrade acetone (5% w/w), followed by filtering of particulate contaminants and subsequent precipitation into deionized water with expression of the rubber curds. The curds are then dried in vacuo to a constant weight. By this or similar procedures, water sorption characteristics of the raw gum are markedly improved. Additionally, swelling of the fully polymerized liner material caused by water sorption in use or during storage can be substantially reduced or eliminated by storing the cured product in a solution of 10% KCl or other similar salt solution.

According to the invention, the fluoroelastomer is preferably cured in the presence of cross-linkers comprising both di- and tri-functional methacrylates such as TMP-TMA, PEGDMA, HGDMA, TEGDMA, or EGDMA which function to decrease water sorption, improve bond strength and tensile strength, and provide sufficient hardness and elongation in the liner material when bonded to the denture base. The cross-linkers are compounded with the fluoroelastomer gum in an amount of from about 5.5% to 25% by weight of difunctional and trifunctional cross-linker based on the weight of total composition, preferably from about 20% to 24%.

In one embodiment of the invention, the liner comprises a dimethacrylate glycol ester, preferably ethylene glycol dimethacrylate (EGDMA), compounded with TMP-TMA and fluoroelastomer in order to improve hardness, tensile and bond strength of the liner product, and to improve workability and packing properties. Generally, an amount of dimethacrylate cross-linking agent of from about 0.5% to about 20%, preferably from about 2% to about 4% (EGDMA), by weight of the total composition is employed, with amounts at the lower end for a soft product and at the higher end for a firm product. The effects on water sorption of fluoroelastomer obtained with a series of methacrylate cross-linking agents, stoichiometrically adjusted for bonding sites, are set forth in Table I. A significant improvement in water sorption characteristics was obtained with TMP-TMA.

TABLE I

| Cross-linker | Amount % | Water Sorption 7 days (%) | 14 days (%) |
|---|---|---|---|
| | (% are percent by weight of composition) | | |
| EGDMA | 8 | 2.19 (w/w %) | 2.36 |
| EGDMA | 13 | 2.88 | 3.32 |
| HGDMA | 8 | 3.61 | 4.30 |
| HGDMA | 13 | 3.83 | 4.62 |
| TMP—TMA | 4 | 4.25 | 5.19 |
| TMP—TMA | 8 | 3.07 | 3.54 |
| TMP—TMA | 13 | 2.25 | 2.63 |
| TMP—TMA | 18 | 1.48 | 1.60 |

The tri-functional cross-linker reduced water sorption further, modestly increased hardness, and increased tensile strength. While EGDMA alone appears to have the opposite effect on water sorption characteristics, EGDMA and similar dimethacrylates improve workability and packing properties and increase strength of the composition of the invention.

A proper balance must be struck between improving mechanical properties and yet retaining adequate softness of the liner material.

The liner composition of the invention further may include filler material homogeneously admixed with the purified fluoroelastomer gum and di- and tri-functional cross-linkers. If a filler is employed, it is first preferably ball-milled with other powdered ingredients, followed by working the powder blend into the fluoroelastomer on a rubber mill. The fluoroelastomer and powdered ingredients are then compounded with di- and tri-functional cross-linker to a smooth, lump-free consistency. Initiator is then added as a solution dissolved in acetone. The material is thereafter stored in a sealed container and in a cool place, preferably under refrigeration. Alternatively, the solid and liquid additives are ball-milled together to a homgeneous mass, and the milled additives then incorporated in the fluoroelastomer gum.

In the composition of the invention, the filler particles significantly increase the strength of the bond between the liner and base owing both to stiffening of the rubber and to the mechanical interlocking of these particles with the liner and base material during curing; the filler additionally improves workability of the composition. Particles comprising beads or fibers are suitable, and it is generally preferable that the particles be compatible with the denture base dough to promote adhesion during the curing process. LUCITONE 199 beads or fibers, obtainable from the L. D. Caulk Company (a division of Dentsply International, Inc.), Milford, Del., are exemplary acrylic particles useful in the composition of the invention. These particles are derived from a hard, grafted poly(methyl methacrylate) resin, and are particularly useful in conjunction with an acrylic denture base dough, such as LUCITONE 199 denture base, a grafted, impact resistant poly(methyl methacrylate) thermoset, similarly obtainable. Other fillers or extenders that may be included comprise hydrophobic amorphous silica of very small particle size. These materials reduce the amount of fluoroelastomer required, increase hardness, improve the ability to grind and polish the cured elastomer, and may improve bond strength. Two examples of these fumed silica fillers/extenders are QUSO WR-542. PQ Corp., Valley Forge, PA, a silica washed with silicone oil, and TULLANOX 500, Tulco, No. Billerica, MA, a silica coated with trimethyl chlorosilane. A particularly useful filler material is particles of barium sulfate, which renders the dental liner opaque to X rays and detectable on radiographs if fragments should be swallowed, inhaled or lost in tne soft tissues of the patient during a traumatic incident.

The amount of filler material employed in the liner composition will vary according to the desired hardness of the finished liner material, as discussed in U.S. Pat. No. 4,432,730, supra. While large amounts of poly(methyl methacrylate) particles (up to 28% by weight of the composition) were found to result in decreased elongation, increased amounts of filler over about 10% by weight of the composition had little effect on bond strength or tensile strength, while effecting a more or less proportional increase in firmness of the finished product. Accordingly, useful amounts of polymeric filler are from about 0% by weight of the composition, for a soft product, to about at least 15% by weight of the composition for a firm product. Preferably, from about 0% to about 10% by weight of inorganic filler is employed for a soft product and about 10-12% by weight for a firm product, depending on which filler is used.

In addition to the filler materials, initiators, and di- and tri-methacrylate cross-linking agents, other components commonlly incorporated into dental liners may be compounded with the fluoroelastomer base. In particular, pigments making the liner more visually acceptable may be used, such as organic pigments, iron oxide-based pigments, and Cd-S-Se pigments.

The uncured liner composition of the invention is a thermosetting putty-like substance that is slightly sticky and moderately elastic. It is readily pressed into shape with finger pressure and will flow well and take excellent detail when molded under an initial pressure of 20.7 MPa or 3000 lbf/in$^2$ in a standard denture flask. At ambient temperatures in excess of 115° F., the composition has a relatively short shelf life (2-4 days). If refrigerated at 2°-7° C. (35°-45° F.), however, shelf life is estimated to be unlimited. Exposure of the unvulcanized composition to air or atmospheric moisture for short periods has no significant deleterious effect. Excess material from trial packing may be recovered and stored in a sealed container again or refrigerated, pending further use.

The curing process, generally done in an open water bath at either 74° C. (165° F.) for eight hours or 74° C. (165° F.) for 1.5 hours followed by 0.5 hours at 100° C. (212° F.), results in an elastomeric material with excellent dimensional stability. Prolonged submersion of the cured elastomer in deionized water will result in some water uptake but only slight dimensional changes result. Selected samples stored in deionized water absorb from 1-3% water (w/w), which then diminish to less than 1% when subsequently stored in 10% KCl solution.

The cured composition shows only slight water sorption and no measurable swelling when stored in 10% KCl.

After curing the liner may be surface-altered using a rough cutting wheel at high speed. It may then be polished by careful use of pumice on a rag wheel. Since the glass transition temperature is very low, cooling of the material has no effect on grinding properties. It is manipulated like any other rubber/sabstrate bonded material and should be ground proceeding from the rubber material toward the hard denture base. It has excellent stain resistance; most stains may be removed by washing in soap and water and lightly scrubbing with a soft bristle brush.

The composite denture of the invention is broadly formed by compounding fluoroelastomer with the components of the dental liner composition as previously described, pressing the resulting composition into a wafer, and molding after removal of a spacer to a denture base dough packed in a customary gypsum mold flask; the composite denture is then heat-treated to cure the liner and the denture base together to provide a lined denture. In an exemplary procedure, a denture waxing is boiled out of a gypsum flask in the usual fashion, and fresh denture base dough is packed. A 1 to 3 mm silicone rubber spacer is placed on the tissue side of the mold cavity, with a polyethylene sheet separator in place, and the denture base dough is trial-packed several times until a satisfactory denture base is produced with no under- or over-extensions. A preliminary cure at 74° C. (165° F.) for 30–45 minutes may be carried out in order to stiffen the denture base so that subsequent packing of the soft liner will not displace the denture base material upon removal of the spacer, after cooling of the flask. methyl methacrylate monomer is then applied with a brush to the denture base in order to thoroughly wet the surface, which will help to achieve a satisfactory bond of the liner to the base. A sheet of the PNF soft liner composition (usually about 10–15 g) is cut to shape and then laid against the base material, and the flask is again trial-packed several times against a thin polyethylene sheet separator. The denture flask is then closed without the separator under pressure (about 20.7 MPa or 3000 psi), and the composite denture is heat-treated to fully cure the base and liner material, for example, by placing the flask in an open water bath (under atmospheric pressure) first at 74° C. (165° F.) for 1.5 hours, and then at 100° C. (212° F.) for up to about 0.5 hours, or for 8 hours at 74° C. (165° F.). The soft denture liner cures via free-radical initiation from the peroxide and addition polymerization of the acrylate cross-linking agents, interpenetrating and also bonding to the few active pendant groups existing as side groups on the PNF molecules.

In one advantageous embodiment of the invention, a wafer of firm liner material is completely laid over the base material dough and trial-packed; the central area of the liner over the alveolar ridge is outlined and cut away. Soft liner material is then laid in the cut-away central area, and the mask is again trial-packed. The composite denture is then heat-cured. This embodiment provides a firm, creep-resistant, higher-strength material at the periphery of the denture which is adjustable, polishable and properly displaces underlying soft tissue, while providing a soft, deformable lower-strength material forming a soft cushion at the center of the denture over the bony structures of the jaw.

Another advantageous embodiment of the invention is the relining of a precured, pre-existing denture in the same fashion as outlined above, thus extending the life of an older denture by renewing its tissue-facing surface with a long-lasting soft denture liner.

EXAMPLE

Preparation of Permanent Soft Denture Liner Formulation

Typically, batches of liner composition are preapred on a six-inch roll mill in 25–100 gram lots. The following procedure is based on a 73.1 g batch:

| Chemical Name | Function | phr | grams | Mfgr. Name | Batch No. |
| --- | --- | --- | --- | --- | --- |
| purified polyphosphazene fluoroelastomer | PNF-200 | 100 | 50 | Firestone | RPP-13750 |
| lauroyl peroxide | initiator | 1 | 0.5 | Polysciences | — |
| $BaSO_4$ | radiopaque filler | 15 | 7.5 | Baker 1030-1 | 117160 |
| trimethylolpropane trimethacrylate | cross-linker | 18 | 9 | Sartomer | 310–713 |
| ethylene glycol dimethacrylate | cross-linker | 2 | 1 | Polysciences | 2303 |
| poly(methyl methacrylate butadiene-styrene | LUCITONE 199 (PMMA beads) | 10 | 5 | Dentsply International | 102183 |
| CdSSe dark red | pigment | 0.2 | 0.1 | Ferro Colors | CP-1880 |

The powdered $BaSO_4$ and PMMA are combined and ball-milled together for several hours. These solids are then added to the PNF gum on the cold roll mill and thoroughly sheared in and blended. To this is then added the TMP-TMA and EGDMA and these ingredients are carefully rolled to form a homogeneous mass.

When the foregoing has been blended to a smooth and lump-free consistency, the peroxide is added as a solution in reagent-grade acetone (typically 0.5 g peroxide in 5–10 ml acetone). Additional acetone may be added to effect homogenization. The material is then milled until the acetone has volatilized as evidenced by absence of acetone odor. This use of an acetone carrier also serves to homogenize all ingredients, avoiding the formation of rubber-rich domains and lumps of agglomerated powder, and to keep the compounded rubber cool during milling and so avoiding premature polymerization by heat-induced free-radical initiation of the peroxide.

The resultant material is then pressed into 15-17 gram "patties" approximately 2 mm thick, 85 mm in diameter, and sealed in a Saran bag. These "patties" are then preferably kept under refrigeration (2°-7° C. or 35°-45° F.) until use.

The PMMA beads (LUCITONE 199) caused the mixture to be very smooth and easily packed into the mold. EGDMA is oily in nature and facilitates the overall milling process. Physical data as shown below were obtained with this formulation.

| Peel Strength | Tensile Strength | Elongation | Modulus (200%) |
|---|---|---|---|
| ~4700 N/m | ~1.9 MPa | ~240% | ~1.8 MPa |
| Durometer A Hardness (Shore A) | | 7 Day H$_2$O Sorption | |
| 35-45 | | ~1.5% (w/w) | |

According to the Example, the powder ingredients are first ball-milled together before blending on a cold rubber mill with the gum rubber; the liquid components are then added and further blended. Finally, the lauroyl peroxide initiator is added in solution with acetone and blended on the mill last. The latter step serves several functions: (a) the chemical initiator is added at the last step where it is less likely to be activated by the heat generated during rolling; (b) the initiator is fully dissolved to achieve complete blending; (c) the acetone functions to break up any lumps of the powdered ingredients which may have survived the ball milling and the roll milling, by dehydrating the lumps and causing the powder particles to repel each other; (d) the entire mixture is homogenized, thus preventing the formation of visible domains of rubber-rich areas; (e) residual water is driven off; and (f) the entire mass is kept cool by evaporation of the acetone during final blending. In the end, all of the acetone is allowed to evaporate before removing the rubber from the mill.

What is claimed is:

1. In a curable denture liner of the type consisting essentially of a phosphonitrilic fluoroelastomer, and at least one dimethacrylate cross-linking agent, the improvement comprising at least one trimethacrylate cross-linking agent.

2. The liner of claim 1 wherein the fluoroelastomer is present in an amount of from about 30% to about 90% by weight, and the dimethacrylate and trimethacrylate are present in a total amount of from about 5.5% to about 24% by weight.

3. The denture liner of claim 2 wherein the fluoroelastomer is characterized by a plurality of repeating units of the general formula

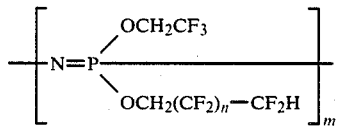

wherein n is 3, 5, 7, 9 or 11 and m is 10,000 to 50,000.

4. The liner of claim 1 further including a filler.

5. The liner of claim 1 further including a free-radical initiator comprising lauroyl peroxide or benzoyl peroxide, wherein the composition is curable under atmospheric conditions at about 100° C. or less.

6. The liner of claim 1, wherein the dimethacrylate cross-linking agent is a glycol ester of dimethacrylic acid, and the trimethacrylate cross-linking agent is trimethylolpropan trimethacrylate.

7. The liner of claim 6 wherein the dimethacrylate cross-linking agent is ethylene glycol dimethacrylate.

8. The liner of claim 7 wherein the ratio of ethylene glycol dimethacrylate to trimethylolpropane trimethacrylate is from about 4:1 to 1:40.

9. The liner of claim 7 wherein the ethylene glycol dimethacrylate is present in an amount of from about 0.5% to 20% by weight of the total composition and the trimethylolpropane trimethacrylate is present in an amount of from about 5% to 20% by weight of the total composition.

10. The liner of claim 6, further including a filler.

11. The liner of claim 10, wherein the filler is present in an amount of from about 10% to about 12%, the ethylene glycol dimethacrylate is present in an amount of from about 2% to about 4% and the trimethylolpropane trimethacrylate is present in an amount of from about 18% to 20%, wherein all amounts are expressed in percent by weight of the composition.

12. The liner of claim 6, wherein the filler comprises particles of a hard acrylic resin.

13. The liner of claim 6, wherein the filler comprises barium sulfate.

14. The liner of claim 4 further including a pigment.

15. A composite denture including a liner comprising the cured liner of claim 1 bonded to a cured denture base material.

16. The composite denture of claim 15 wherein the denture base material is primarily a poly(methyl methacrylate) denture base.

17. The composite denture of claim 15, wherein the liner and denture base material are cured together to bond the liner to the denture base.

18. The composite denture of claim 15, wherein the liner comprises a fluoroelastomer compounded with a glycol ester of dimethacrylic acid and trimethylolpropane trimethacrylate.

19. The composite denture of claim 18, wherein the liner further includes a filler.

20. The composite denture of claim 15, wherein the composition is curable under atmospheric conditions in a closed denture flask at about 100° C., or less.

21. The composite denture of claim 18, wherein the glycol ester of dimethacrylic acid is ethylene glycol dimethacrylate.

22. The composite denture of claim 18, wherein the ratio of trimethacrylate to dimethacrylate in the liner is from about 40:1 to about 1:4.

23. A method for forming a substantially non-toxic composite denture of claim 15 of improved physical characteristics comprising:
(a) lining denture base material with a denture liner comprising a phosphonitrilic fluoroelastomer, at least one dimethacrylate cross-linking agent and at least one trimethacrylate cross-linking agent curable at a temperature of 100° C. or less under atmospheric pressure; and
(b) subjecting the lined denture base material to a temperature of about 100° C. or less at atmospheric pressure to cure the denture liner and bond the liner to the denture base material to form a composite denture.

24. The method of claim 23 wherein the fluoroelastomer is characterized by a plurality of repeating units of the formula

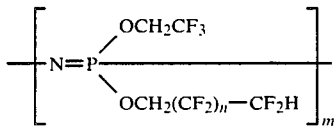

wherein n is 3, 5, 7, 9 or 11, and m is between 10,000 and 50,000.

25. The method of claim 23, wherein the surface of the curable denture base material is wetted with a $C_1$–$C_6$ alkyl monomethacrylate monomer before lining with the dentur liner material.

26. The method of claim 23, wherein the trimethacrylate is trimethlolpropane trimethacrylate.

27. The method of claim 26 wherein the dimethacrylate is a glycol ester of dimethacrylic acid.

28. The method of claim 23, wherein the liner further includes a free-radical initiator.

29. The method of claim 27 wherein the glycol ester of dimethacrylic acid is a polyethylene glycol ester, a 1,6-hexamethylene glycol ester, an ethylene glycol ester, or a tetraethylene glycol ester.

30. The method of claim 23, wherein the liner further includes a filler.

31. The method of claim 29 wherein the glycol ester of dimethacrylic acid is ethylene glycol dimethacrylate.

32. The method of claim 30, wherein the filler comprises particles of a hard acrylic resin, or $BaSO_4$, or both.

33. The method of claim 23, wherein the denture base material is primarily a poly(methyl methacrylate) denture base dough.

34. The method of claim 28, wherein the initiator is lauroyl peroxide or benzoyl peroxide.

35. The method of claim 23, wherein the denture base material of paragraph (a) is precured before lining with the denture liner.

36. The method of claim 23, wherein the denture base material of paragraph (a) is a curable denture base material which is concurrently cured with the denture liner to bond the liner and denture base material together in accordance with paragraph (b).

37. The method of claim 35, wherein the precured denture base is a pre-existing denture.

38. The liner of claim 9, wherein the dimethcrylate is present in an amount of from about 2 to 4% by weight and the trimethacrylate is present in an amount of from about 18 to 20% by weight.

* * * * *